(12) United States Patent
Harris et al.

(10) Patent No.: US 9,040,485 B2
(45) Date of Patent: *May 26, 2015

(54) SYNTHETIC ANALOGUES OF NEURAL REGENERATION PEPTIDES

(71) Applicant: Curonz Holdings Company Limited, Auckland (NZ)

(72) Inventors: Paul William Richard Harris, Waitakere (NZ); Margaret Ann Brimble, Auckland (NZ); Frank Sieg, Auckland (NZ)

(73) Assignee: CURONZ HOLDINGS COMPANY LIMITED, AUCKLAND (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/651,884

(22) Filed: Oct. 15, 2012

(65) Prior Publication Data

US 2013/0231289 A1 Sep. 5, 2013

Related U.S. Application Data

(63) Continuation of application No. 12/754,937, filed on Apr. 6, 2010, now Pat. No. 8,309,684, and a continuation of application No. PCT/US2008/011951, filed on Oct. 17, 2008.

(60) Provisional application No. 60/999,292, filed on Oct. 17, 2007, provisional application No. 60/999,503, filed on Oct. 18, 2007.

(51) Int. Cl.
| | |
|---|---|
| *A01N 37/18* | (2006.01) |
| *A61K 38/00* | (2006.01) |
| *C07K 7/08* | (2006.01) |
| *C07K 14/48* | (2006.01) |
| *C07K 7/06* | (2006.01) |

(52) U.S. Cl.
CPC .......... *C07K 7/08* (2013.01); *G01N 2800/2878* (2013.01); *G01N 2800/2892* (2013.01); *G01N 2800/2835* (2013.01); *G01N 2800/28* (2013.01); *G01N 2800/285* (2013.01); *A61K 38/00* (2013.01); *C07K 14/48* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 8,138,304 B2 | 3/2012 | Sieg et al. | 514/12 |
| 8,309,684 B2 * | 11/2012 | Harris et al. | 530/327 |
| 2004/0180823 A1 | 9/2004 | Pasquale et al. | |
| 2005/0131212 A1 | 6/2005 | Sieg et al. | |

FOREIGN PATENT DOCUMENTS

WO  WO 2006/121926 A2  11/2006  ........ C07K 14/705

* cited by examiner

*Primary Examiner* — Olga N Chernyshev
(74) *Attorney, Agent, or Firm* — Nixon & Vanderhye P.C

(57) ABSTRACT

Embodiments of this invention include synthetic compounds (NRP analogues) of peptides termed neural regeneration peptides (NRPs). NRP analogues are made by substituting amino acids in the native peptide sequence, modifying amino acids chemically, by replacing amino acids with synthetic moieties, by stabilizaing β-turns, acetylation of terminal glycine residues or by cyclization. NRP analogues can be used to treat a variety of conditions involving degeneration of neural cells, and includes treating disorders of the nervous system, including peripheral neuropathy, multiple sclerosis, diabetic peripheral neuropathy, neurotoxin-induced neurodegeneration, and amyotrophic lateral sclerosis.

3 Claims, 8 Drawing Sheets

SYNTHETIC ANALOGUES OF NEURAL REGENERATION PEPTIDES

CROSS-REFERENCE TO RELATED APPLICATIONS

This application is a continuation of application Ser. No. 12/754,937 filed Apr. 6, 2010, U.S. Pat. No. 8,309,684, which is a continuation of PCT/US2008/011951 filed Oct. 17, 2008, which claims benefit of Provisional Application Nos. 60/999,292 filed Oct. 17, 2007 and 60/999,503 filed Oct. 18, 2007, the entire contents of each of which are hereby incorporated by reference.

CLAIM OF PRIORITY

This PCT International application claims priority to U.S. Provisional Application No. 60/999,292 entitled "Synthetic Analogs of Neural Regeneration Peptides," filed Oct. 17, 2007, and to U.S. Provisional Patent Application No. 60/999,503, entitled "Synthetic Analogs of Neural Regeneration Peptides," filed Oct. 18, 2007. Both of these provisional applications are incorporated herein fully by reference as if individually so incorporated.

FIELD OF THE INVENTION

This invention relates to synthetic analogues of peptides that have neural regeneration, migration, proliferation, differentiation and/or axonal outgrowth properties. These peptides are termed "Neural Regeneration Peptides" or "NRPs." In particular, this invention relates to analogues of relatively small peptides that have one or more biological properties of NRPs.

BACKGROUND

Neural regeneration peptides (NRPs) are a class of peptides that have been shown to exhibit properties desirable for promoting neural function in mammals These functions include neural survival, neural proliferation, neuronal outgrowth, neural migration and neuronal differentiation. Several NRPs have been previously described, and include those disclosed in U.S. patent application Ser. Nos. 10/225,838 and 10/976,699, PCT/US02/026782, PCT/US2004/036203, PCT/US2006017534 and PCT/US2006026994. Each of the above patent applications is expressly incorporated herein fully by reference as if individually so incorporated.

SUMMARY

NRPs described to date have desirable pharmacodynamic properties and promote neural regeneration, migration, proliferation, differentiation and/or axonal outgrowth. We have recently discovered synthetic NRP analogues that also have improved pharmacokinetic properties. There is a need in the art for synthetic molecules or modified peptides that have desirable pharmacodynamic properties similar to those of NRPs but also have improved pharmacokinetic properties and/or are chemically stable.

Certain aspects of this invention include novel synthetic NRP analogue molecules that can be used to treat disorders of the nervous system or other systems in which NPRs is effective. Another aspect is to provide therapies for disorders of cellular degeneration and death, including certain nervous system disorders. In some aspects, synthetic analogues of NRPs can be used to treat adverse effects of amyotrophic lateral sclerosis (ALS), multiple sclerosis (MS), oxidative stress (e.g., Huntington's disease) or peripheral neuropathy (PN). An additional aspect of this invention is the production of NRP analogues with improved stability.

It should be understood that the terms "NRP compound," "analogue of NRP" "SEQ ID NO:" and other such terms, for simplicity, are used to identify the molecules of the invention and not to provide their complete characterization. Thus, an "analogue of NRP" may be characterized herein as having a particular amino acid sequence, a particular 2-dimensional representation of the structure, but it is understood that the actual molecule claimed has other features, including 3-dimensional structure, mobility about certain bonds and other properties of the molecule as a whole. It is the molecules themselves and their properties as a whole that are the subjects of this invention.

It should also be understood that the designation of a peptide as an "NRP" does not mean that it solely has neural effects. Rather, the term NRP is intended to include peptides having similar structural components as described in the above patent applications, but may have effects on other cell types, tissues, and/or organs. In certain embodiments, analogues of relatively short NRPs are provided that can have increased stability, due at least in part to decreased enzymatic degradation. In other embodiments, NRP analogues are provided having modified amino acids. In yet further embodiments, NRP analogues are provided that have non-amino acid substituents replacing amino acids.

BRIEF DESCRIPTION OF THE FIGURES

This invention will be described with reference to specific embodiments thereof. Other features and aspects of this invention can be appreciated by reference to the Figures, in which.

DETAILED DESCRIPTION

In some embodiments, NRP compounds are provided that have a sequence of a native peptide. For example, one such NRP is an 11 amino acid long (11-mer) peptide having the following sequence.

SEQ ID NO: 1
NH$_2$-G$^1$RRAAPGRAGG$^{11}$-NH$_2$

It should be appreciated that synthetic compounds or analogues of NRPs can have either amidated C-termini or can have C-terminal hydroxyl residues (OH). It should also be appreciated that the terms "NRP compound," "NRP analogue" and similar terms refer to compounds of this invention or to previously disclosed NRP peptides or NRP proteins.

Synthetic Analogues of NRPs

Synthetic analogues of NPRs are provided that can have one or more of the following types of modifications: (1) stabilization of β-turns, (2) replacement of glycine residues, (3) replacement of the N-terminal glycine residue and/or (4) cyclization.

1. Stabilization of β-Turns

Chou and Fasman probabilities for β-turn prediction reveal that probable β-turns in SEQ ID NO:1 can be found in the domains APGR (SEQ ID NO:2) and RAGG (SEQ ID NO:3), as shown in bold below:

SEQ ID NO: 1
SEQ ID NO: 1. NH$_2$-G$^1$RRAAPGRAGG$^{11}$-NH$_2$

β-turns can be stabilised by introducing steric constraints such as alkylated amino acids. Readily available amino acids that can be used include aminoisobutyric acid (Aib, α-H on alanine replaced with methyl) can be used as a replacement for either or both of alanine and glycine residues.

A. Modification of the APGR Domain

In sequence APGR (SEQ ID NO: 2), the alanine or glycine can be replaced with aminoisobutyric acid (Aib). Substitution of the alanine with Aib produces the following analogue:

SEQ ID NO: 4
NH$_2$-G$^1$RRA-Aib-PGRAGG$^{11}$-NH$_2$

B. Modification of the RAGG Domain

In another probable β-turn sequence, RAGG (SEQ ID NO: 3), the alanine can be replaced with aminoisobutyric acid (Aib) to produce the analogue having the sequence:

SEQ ID NO: 5
NH$_2$-G$^1$RRAAPGR-Aib-GG$^{11}$-NH$_2$

Figure 7:
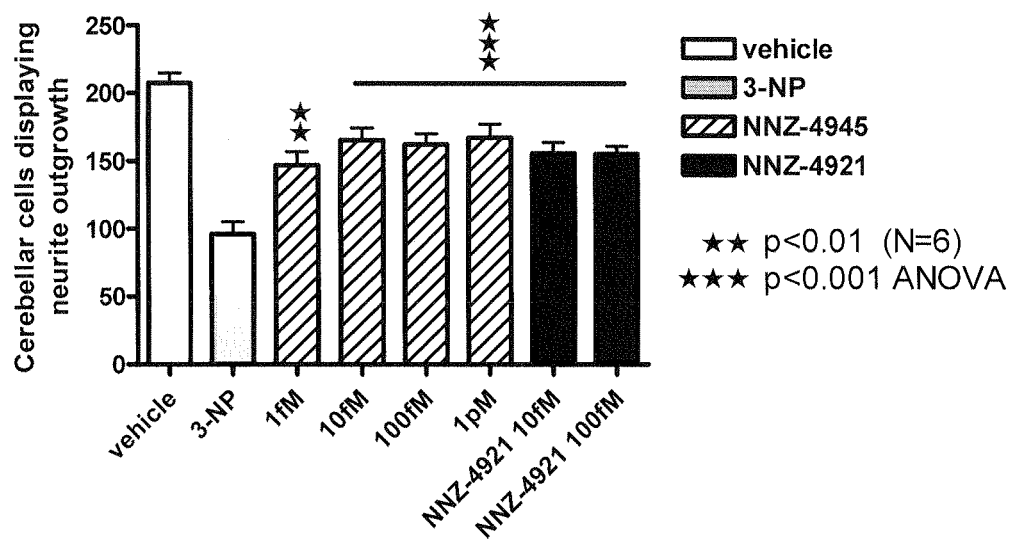
FIG. 7 depicts a graph of results of beam walking scores for rats with peripheral neuropathy induced by pyridoxine (1200 mg/kg) and treated with either vehicle or SEQ ID NO:5 of this invention.
Figure 8:
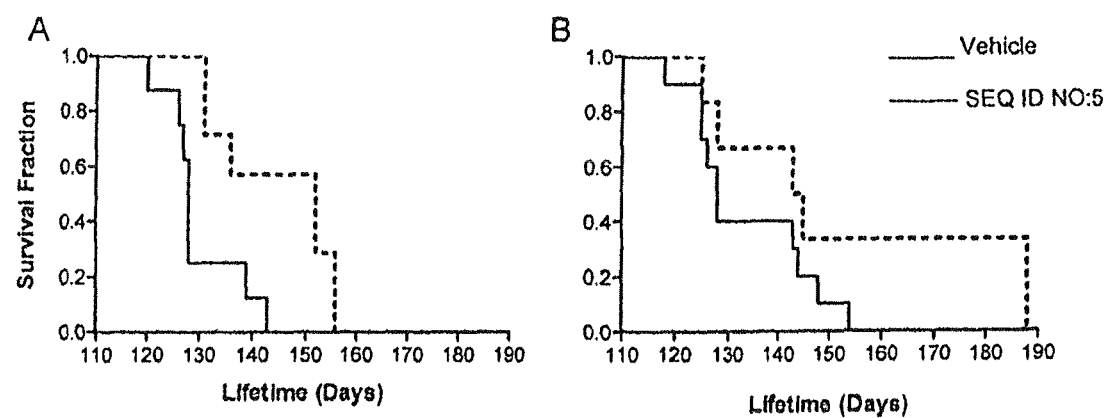
FIG. 8 depicts graphs of results of studies of longevity of mice with a murine model of amytrophic lateral sclerosis (ALS) and the effects of two different doses of a synthetic NRP of this invention, SEQ ID NO:5.

Experiments showed that SEQ ID NO:5 was: neuroprotective (see FIGS. 1-4), stable under storage conditions (FIGS. 2 and 3), more neuroprotective than the unsubstituted NRP (FIGS. 1 and 4), peripheral neuropathy (FIGS. 6 and 7) and ALS (FIG. 8).

2. Replacement of Glycine Residues

Replacement of the internal glycine residue by an asparagine (N) can induce β-turns due to asparagine having higher β-turn propensity than glycine. Therefore the internal glycine residue can be replaced with asparagine at amino acid position 10 producing a peptide having the following sequence:

SEQ ID NO: 6
NH$_2$-G$^1$RRAAPGRANG$^{11}$-NH$_2$

This NRP analogue was found to be neuroprotective in in vitro model of neural toxicity induced by 3-NP.

3. Replacement of the N-Terminal Glycine Residue

Truncation of the G$^1$ at the N terminus can result in loss of biological activity. Replacement of the G$^1$ with an acetyl group can restore biological activity. The resulting NRP analogue is acetylated providing a peptide having the following sequence:

SEQ ID NO: 7
AcNH-RRAAPGRAGG$^{11}$-NH$_2$

This NRP analogue was found to be neuroprotective in the face of toxicity induced by 3-NP.

4. Replacement of L-Amino Acids with D-Amino Acids The secondary structure of a peptide can be affected by the presence of D-amino acids replacing one or more L-amino acids (naturally occurring). Replacement of the third amino acid from the N-terminus produces a compound having the following sequence:

SEQ ID NO: 8
NH$_2$-GR (D-Arg) AAPGRAGG-NH$_2$

This NRP analogue was found to be neuroprotective in the in vitro model of neural toxicity induced by 3-NP.

5. Cyclization

Synthesis of a cyclic peptide mimetic of SEQ ID NO:1 can be carried out. One method involves adding a cysteine residue to each end of the sequence, and then oxidizing the resultant product to produce a cyclic disulfide having the following sequence:

SEQ ID NO: 9
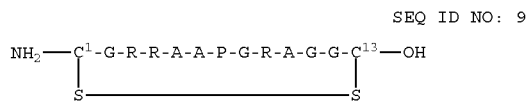

Alternatively, both the N and C terminal glycine residues can be replaced with a cysteine residue and oxidized similarly as above, producing an analogue having the following sequence.

SEQ ID NO: 10
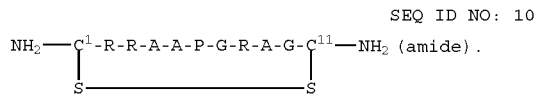

Direct cyclization of the C terminal residue to the N terminal residue can be accomplished by creating an amide bond to produce a peptide having the following sequence.

SEQ ID NO: 11

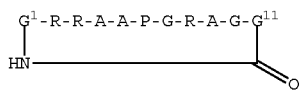

The use of circular dichroism can indicate secondary structure and the use of computer simulation software for the modeling of small peptides can also be carried out using conventional methods. Both of these techniques can be used for determining structural features of the NRP analogues of this invention.

Synthesis of Synthetic Analogues of NRPs

Starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic α-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. each article herein expressly incorporated herein fully by reference.

Conveniently, synthetic production of the polypeptides of the invention may be according to the solid-phase synthetic method described by Goodman M. (ed.), "Synthesis of Peptides and Peptidomimetics" in Methods of organic chemistry (Houben-Weyl) (Workbench Edition, E22a, b, c, d, e; 2004; Georg Thieme Verlag, Stuttgart, New York)., herein expressly incorporated fully by reference. This technique is well understood and is a common method for preparation of peptides. The general concept of this method depends on attachment of the first amino acid of the chain to a solid polymer by a covalent bond. Succeeding protected amino acids are added, on at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_2$), and phenylmethoxycarbonyl (Z or CBZ). Additional protective groups are identified in Goodman, cited above, as well as in McOmie J F W: Protective Groups in Organic Chemistry, Plenum Press, New York, 1973, both references expressly incorporated fully herein by reference.

General procedures for preparing peptides of this invention involve initially attaching a carboxyl-terminal protected amino acid to the resin. After attachment the resin is filtered, washed and the protecting group on the alpha-amino group of the carboxyl-terminal amino acid is removed. The removal of this protecting group must take place, of course, without breaking the bond between that amino acid and the resin. The next amino, and if necessary, side chain protected amino acid, is then coupled to the free amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Peptides may be cyclized by the formation of a disulfide bond between two cysteine residues. Methods for the formation of such bonds are well known and include such methods as those described in G. A. Grant (Ed.) Synthetic Peptides A User's Guide $2^{nd}$ Ed., Oxford University Press, 2002, W. C. Chan and P. D. White (Eds.) Fmoc Solid Phase Synthesis A Practical Approach, Oxford University Press, 2000 and references therein.

Alternative techniques for peptide synthesis are described in Bodanszky et al, Peptide Synthesis, 2nd ed, John Wiley and Sons, New York, 1976, expressly incorporated herein fully by reference. For example, the peptides of the invention may also be synthesized using standard solution peptide synthesis methodologies, involving either stepwise or block coupling of amino acids or peptide fragments using chemical or enzymatic methods of amide bond formation (see, e.g. H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.) These solution synthesis methods are well known in the art.

Commercial peptide synthesizers, such as the Applied Biosystems Model 430A, are available for the practice of these methods.

Therapeutic Uses of NRP Analogues

NRP analogues of this invention can be used to treat neurological disorders. NPRs have been unexpectedly effective in treating neural degeneration associated with autoimmune disorders of the brain, including EAE and multiple sclerosis (MS), amyotrophic lateral sclerosis (ALS) and toxic injury to neural cells.

Disorders and Conditions Treatable with NRP Analogues

Disorders and conditions in which NRP compounds of this invention can be of benefit include the following.

Nervous system conditions treatable with NRP analogues include infections of the central nervous system including bacterial, fungal, spirochetal, parasitic and sarcoid including pyrogenic infections, acute bacterial meningitis or leptomeningitis.

Cerebrovascular diseases include stroke, ischemic stroke, hypoxia/ischemia, atherosclerotic thrombosis, lacunes, embolism, hypertensive haemorrhage, ruptured aneurysms, vascular malformations, transient ischemic attacks, intracranial haemorrhage, spontaneous subarachnoid haemorrhage, hypertensive encephalopathy, inflammatory diseases of the brain arteries, decreased perfusion caused by, for example, cardiac insufficiency (possibly resulting from coronary bypass surgery) and other forms of cerebrovascular disease.

Craniocerebral traumas include basal skull fractures and cranial nerve injuries, carotid-cavernous fistula, pneumocephalus, aerocele andrhinorrhea, cerebral contusion, traumatic intracerebral haemorrhage, traumatic brain injury, penetrating traumatic brain injury and acute brain swelling in children.

Demyelinating diseases include neuromyelitis optica, acute disseminated encephalomyelitis, acute and subacute necrotizing haemorrhagic encephalitis, diffuse cerebral sclerosis of Schilder and multiple sclerosis in conjunction with peripheral neuropathy. Degenerative diseases of the nervous system including syndrome of one or more of progressive dementia, diffuse cerebral atrophy, diffuse cortical atrophy of the non-Alzheimer type, Lewy body dementia, Pick's disease, fronto-temporal dementia, thalamic degeneration, non-Huntingtonian types of Chorea and dementia, cortico-spinal degeneration (Jakob), the dementia-Parkinson-amyotrophic lateral sclerosis complex (Guamanina and others) and amyotrophic lateral sclerosis (ALS).

Peripheral neuropathies are common and disabling conditions characterised by damage to or loss of peripheral neurons. There are more than 100 types of peripheral neuropathy, each with its own characteristic set of symptoms, pattern of development, and prognosis. Peripheral neuropathy may be either inherited or acquired. Inherited forms of peripheral neuropathy can be caused by genetic mutations. Some types of peripheral neuropathy and features common to them are shown below in Table 1. Table 1 above shows comparisons between pyridoxine-, streptozotin- and chemotherapy-induced peripheral neuropathy and diabetic peripheral neuropathy.

TABLE 1

Features Common to Peripheral Neuropathies

| | Pyridoxine (Vitamin B6) Intoxication | Streptozotocin-Induced Diabetic Neuropathy | Diabetic Peripheral Neuropathy | Chemotherapy-Induced Peripheral Neuropathy |
|---|---|---|---|---|
| Model/Condition | Experimental Model & Clinical Condition | Experimental Model | Clinical Condition | Experimental Model & Clinical Condition |
| Principle Pathology | Reversible peripheral nerve axonopathy, resulting in reduced sensory fiber conduction velocity, restricted to large diameter cells, without demyelination. [1, 2, 3, 4, 5, 6] | Peripheral nerve axonopathy, resulting in reduced autonomic and sensory fiber conduction velocity, with degeneration being fiber length dependent. [11, 12, 13] | Progressive peripheral nerve axonopathy, resulting in reduced sensory fiber conduction velocity, with degeneration being fiber length dependent. [19, 20, 21] | Peripheral nerve neuronopathy, as well as damage to dorsal root ganglia, resulting in reduced sensory fiber conduction velocity, with and without demyelination. [22, 23] |
| Proposed Mechanism of Toxicity | Saturation of pyridoxal kinase in the liver may inhibit neuronal pyridoxal phosphate, altering neuronal metabolism. Impaired neuronal metabolism leads to an impoverished energy support of the large axons. [2, 3] | Selective toxicity to islet β-cells of the pancreas leading to a hyperglycemic diabetic condition, with resulting neurotoxicity, as in clinical diabetes. [14, 15, 16] | Wallerian axonal degeneration resulting from hyperglycemic neurotoxicity. Raised glucose favors metabolism through the polyol pathway that results in production of oxidative stress. [16, 19, 20] | (For platinum compounds) Disturbance of metabolism and axonal transport in peripheral sensory nerves following accumulation in the DRG leads to axonopathy. [22, 24] |
| Peripheral Nerves Affected | Primarily large descending sensory nerves, including peroneal and sural nerves that descend from the sciatic. [3, 6, 7] | Primarily autonomic and sensory nerves, including peroneal and other nerves descending from the sciatic. [11, 13] | Primarily large descending sensory nerves, including peroneal and sural nerves that descend from the sciatic. [19, 20] | Primarily large descending sensory nerves, including peroneal and sural nerves that descend from the sciatic. [22, 23] |
| Functional Outcomes | Motoric impairment of hind-limbs due to loss of sensory feedback, particularly from the hind limbs. [3, 6, 7, 8, 9, 10] | Predominantly positive symptoms of hyperalgesia/allodynia. [17, 18] | Initially positive symptoms of pain or paresthesia, then progressing to negative symptoms with loss of sensory feedback, particularly from the feet. [19, 20] | Sensory neuronopathy, with diminished vibration perception, paresthesia, loss of tendon reflex, pain and, later, ataxia (motoric impairment). [22, 23] |

Acquired peripheral neuropathy may result from: physical injury (trauma) to a nerve, tumors, toxins (including chemotherapy), autoimmune responses, nutritional deficiencies, alcoholism, vascular and metabolic disorders (e.g. diabetic neuropathy). The HIV-associated peripheral neuropathy is a common side effect of drugs targeting the reverse transcriptase of the HIV virus. The symptoms of peripheral neuropathy can vary from temporary numbness, tingling, and pricking sensations, sensitivity to touch or muscle weakness, to more extreme symptoms such as burning pain, muscle wasting, paralysis, organ or gland dysfunction.

The first report of a human sensory neuropathy induced by a high dose of pyridoxine (vitamin B6) derives from Schaumberg et al., *New Eng. J. Medicine* 309:445-448, 1983. Daily intakes were in the 2000-6000 mg/day range over periods from 2 to 14 months. All patients displayed a "stocking-glove" sensory loss with numbness in hands, feet and an unstable gait.

Using rat models of peripheral neuropathy enables the examination of neurological abnormalities induced by pyridoxine. For instance, 1,200 or 800 mg/kg/day of pyridoxine administered to rats for 5-10 days results in necrosis of sensory neurons, especially affecting large diameter neurons in the sciatic nerve and the dorsal root ganglion (Xu et al., *Neurology* 39:1077-1083, 1989).

Pyridoxine-induced peripheral neuropathy in animals is a recognized system for studying effects of therapeutic agents. In particular, this system is predictive of effects of such agents on peripheral neuropathy in human beings.

Metabolic Disorders

Acquired metabolic disorders of the nervous system including metabolic diseases presenting as a syndrome comprising one or more of confusion, stupor or coma-ischemia-hypoxia, hypoglycaemia, hyperglycemia, hypercapnia, hepatic failure and Reye syndrome, metabolic diseases presenting as a progressive extrapyramidal syndrome, metabolic diseases presenting as cerebellar ataxia, hyperthermia, celiac-sprue disease, metabolic diseases causing psychosis or dementia including Cushing disease and steroid encephalopathy, thyroid psychosis and hypothyroidism and pancreatic encephalopathy. An example of a metabolic disorder that can result in neuropathy is pyridoxine excess described more fully below.

Diseases of the Nervous System Due to Nutritional Deficiency, Alcohol and Alcoholism Disorders of the nervous system due to drugs and other chemical agents include opiates and synthetic analgesics, sedative hypnotic drugs, stimulants, psychoactive drugs, bacterial toxins, plant poisons, venomous bites and stings, heavy metals, industrial toxins, anti-neoplastic and immunosuppressive agents, thalidomide, aminoglycoside antibiotics (ototoxicity) and penicillin derivatives (seizures), cardioprotective agents (beta-blockers, digitalis derivatives and amiodarone).

As illustrated by the preceding list, compositions and methods of the invention can find use in the treatment of human neural injury and disease. Still more generally, the compositions and methods of the invention find use in the treatment of human patients suffering from neural damage as the result of acute brain injury, including but not limited to diffuse axonal injury, perinatal hypoxic-ischemic injury, traumatic brain injury, stroke, ischemic infarction, embolism, and hypertensive haemorrhage; exposure to CNS toxins, infections of the central nervous system, such as, bacterial meningitis; metabolic diseases such as those involving hypoxic-ischemic encephalopathy, peripheral neuropathy, and glycogen storage diseases; or from chronic neural injury or neurodegenerative disease, including but not limited to Multiple Sclerosis, Lewy Body Dementia, Alzheimer's disease, Parkinson's disease and Huntington's disease. Patient's suffering from such diseases or injuries may benefit greatly by a treatment protocol able to initiate neuronal proliferation and migration, as well as neurite outgrowth.

Still more generally, the invention has application in the induction of neuronal and neuroblast migration into areas of damage following insult in the form of trauma, toxin exposure, asphyxia or hypoxia-ischemia.

Administration of NRP Analogues

NRP analogues can be used via direct administration to the patient. An NRP analogue can be administered as part of a medicament or pharmaceutical preparation. This can involve combining an NRP analogue with any pharmaceutically appropriate carrier, adjuvant or excipient. Additionally an NRP analogue can be used with other non-NRP neuroprotective, proliferative, or other agent. The selection of the carrier, adjuvant or excipient can depend upon the route of administration to be employed.

The administration route can vary widely to suit a particular condition. An NRP analogue may be administered in different ways: intraperitoneally, intravenously or intracerebroventricularly. The peripheral application may be a route of choice because then there is no direct interference with the central nervous system.

Any peripheral route of administration known in the art can be employed. These can include parenteral routes for example injection into the peripheral circulation, subcutaneous, intraorbital, ophthalmic, intraspinal, intracisternal, topical, infusion (using eg. slow release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (eg. amounts which eliminate or reduce the patient's pathological condition) to provide therapy for the neurological diseases described above.

One route of administration includes subcutaneous injection (e.g., dissolved in 0.9% sodium chloride) and oral administration (e.g., in a capsule).

It will also be appreciated that it may on occasion be desirable to directly administer NRP analogue to the CNS of the patient by any appropriate route of administration. Examples include administration by lateral cerebroventricular injection or through a surgically inserted shunt into the lateral cerebral ventricle of the brain of the patient, into the cerebrospinal fluid or directly into an affected portion of a patient's brain.

Therapeutic Doses of NRP Analogues

In some embodiments of this invention, methods for treating brain damage comprise administering one or more NRP analogues in a dose range of from about 0.01 μg/kg body weight to about 100 μg/kg body weight. In other embodiments, a dose of 1 μg/kg body weight to about 10 μg/kg body weight can be useful. In further embodiments, a dose of an NRP can be in the range of about 0.01 μg/kg body weight to about 0.1 mg/kg.

In other embodiments, the determination of an effective amount of an NRP analogue to be administered is within the skill of one of ordinary skill in the art, and will be routine to those persons skilled in the art. In certain embodiments, the amount of an NRP analogue to be used can be estimated by in vitro studies using an assay system as described herein. The final amount of an NRP analogue to be administered will be dependent upon the route of administration, upon the NRP analogue used and the nature of the neurological disorder or condition that is to be treated. A suitable dose range may for example, be between about 0.01 µg to about 15 µg per 1 kg of body weight or in other embodiments, about 20 µg/kg to about 30 µg/kg body weight per day.

For inclusion in a medicament, NRP analogue can be directly synthesized by conventional methods such as the stepwise solid phase synthesis method of Merrifield et al., 1963 (J. Am. Chem. Soc. 15:2149-2154) or Goodman M. (ed.), "Synthesis of Peptides and Peptidomimetics" in Methods of organic chemistry (Houben-Weyl) (Workbench Edition, E22a, b, c, d, e; 2004; Georg Thieme Verlag, Stuttgart, New York), expressly incorporated herein fully by reference. Such methods of peptide synthesis are known in the art, and are described, for example, in Fields and Colowick, 1997, *Solid Phase Peptide Synthesis* (Methods in Enzymology, vol. 289), Academic Press, San Diego, Calif., expressly incorporated herein fully by reference. Alternatively synthesis can involve the use of commercially available peptide synthesizers such as the Applied Biosystems model 430A.

As a general proposition, the total pharmaceutically effective amount of an NRP analogue administered parenterally per dose will be in a range that can be measured by a dose response curve. For example, an NRP analogue in the blood can be measured in body fluids of the mammal to be treated to determine dosing. Alternatively, one can administer increasing amounts of an NRP compound to the patient and check the serum levels of the patient for the NRP analogue. The amount of NRP analogue to be employed can be calculated on a molar basis based on these serum levels of the NRP analogue.

One method for determining appropriate dosing of the compound entails measuring NRP levels in a biological fluid such as a body or blood fluid. Measuring such levels can be done by any means, including RIA and ELISA. After measuring NRP analogue levels, the fluid is contacted with the compound using single or multiple doses. After this contacting step, the NRP analogue levels are re-measured in the fluid. If the fluid NRP analogue levels have fallen by an amount sufficient to produce the desired efficacy for which the molecule is to be administered, then the dose of the molecule can be adjusted to produce maximal efficacy. This method can be carried out in vitro or in vivo. This method can be carried out in vivo, for example, after the fluid is extracted from a mammal and the NRP analogue levels measured, the compound herein is administered to the mammal using single or multiple doses (that is, the contacting step is achieved by administration to a mammal) and then the NRP analogue levels are re-measured from fluid extracted from the mammal.

NRP analogues are suitably administered by a sustained-release system. Suitable examples of sustained-release compositions include semi-permeable polymer matrices in the form of shaped articles, for example, films, or microcapsules. Sustained-release matrices include polylactides (U.S. Pat. No. 3,773,919, EP 58,481), poly(2-hydroxyethyl methacrylate) (Langer et al., 1981), ethylene vinyl acetate (Langer et al., supra), or poly-D-(−)-3-hydroxybutyric acid (EP 133, 988). Sustained-release compositions also include a liposomally associated compound. Liposomes containing the compound are prepared by methods known to those of skill in the art, as exemplified by DE 3,218,121; Hwang et al., 1980; EP 52,322; EP 36,676; EP 88,046; EP 143,949; EP 142,641; Japanese Pat. Appln. 83-118008, U.S. Pat. Nos. 4,485,045 and 4,544,545 and EP 102,324. In some embodiments, liposomes are of the small (from or about 200 to 800 Angstroms) unilamellar type in which the lipid content is greater than about 30 mol. percent cholesterol, the selected proportion being adjusted for the most efficacious therapy. All U.S. parents referred to herein, both supra and infra, are hereby expressly incorporated by reference in their entirety.

PEGylated peptides having a longer life than non-PEGylated peptides can also be employed, based on, for example, the conjugate technology described in WO 95/32003 published Nov. 30, 1995.

In some embodiments, the compound can be formulated generally by mixing each at a desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. It can be appreciated that the above doses are not intended to be limiting. Other doses outside the above ranges can be determined by those with skill in the art.

In some embodiments, formulations can be prepared by contacting a compound uniformly and intimately with liquid carriers or finely divided solid carriers or both. Then, if desired, the product can be shaped into the desired formulation. In some embodiments, the carrier is a parenteral carrier, alternatively, a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are desirably non-toxic to recipients at the dosages and concentrations employed, and include, by way of example only, buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, and the like. In certain embodiments, a peptide of this invention can be stabilized using 0.5 M sucrose or 0.5 M trehalose. Using such sugars can permit long-term storage of the peptides.

An NRP compound can be desirably formulated in such vehicles at a pH of from about 6.5 to about 8. Alternatively, the pH can be from about 4.5 to about 8. It will be understood that use of certain of the foregoing excipients, carriers, or stabilizers will result in the formation of salts of the compound. The final preparation may be a stable liquid or lyophilized solid.

In other embodiments, adjuvants can be used. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Desirably, an NRP analogue to be used for therapeutic administration may be sterile. Sterility can be readily accomplished by filtration through sterile filtration membranes (e.g., membranes having pore size of about 0.2 micron). Therapeutic compositions generally can be placed into a container having a sterile access port, for example an intravenous solution bag or vial having a stopper pierceable by a hypodermic injection needle.

In other embodiments, an NRP analogue can be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 0.01% (w/v) aqueous solution of compound, and the resulting mixture is lyophilized The infusion solution can be prepared by reconstituting lyophilized compounds using bacteriostatic water or other suitable solvent.

In still further embodiments, a kit may contain a predetermined amount of lyophilized NRP compound, a physiologically compatible solution for preparation of a dosage form, a mixing vial, a mixing device, and instructions for use. Such kits can be manufactured and stored according to usual practices in the industry.

An NRP compound-containing composition may be administered by one or more of a variety of routes. By way of example, intravenous, intraperitoneal, intracerebral, intraventricular, inhalation, lavage, rectal, vaginal, transdermal, subcutaneous administration can be used.

EXAMPLES

The following examples are presented to illustrate specific embodiments of this invention. Persons of ordinary skill can utilize the disclosures and teachings herein to produce other embodiments and variations without undue experimentation. All such embodiments and variations are considered to be part of this invention.

Example 1

Effects of NRP Compounds on Survival and Proliferation of Cerebellar Microexplants NRP Compound Preparation NRP compounds were provided by Auspep (Australia). The peptides were synthesized using standard solid-phase synthesis. The peptides were supplied with an amidated C-terminus, and were more than 95% pure as analyzed by MALDI-MS spectrum analysis. The peptides were stored lyophilized at −80° C. under argon in 0.5M sucrose or 0.5M trehalose until usage. They were reconstituted in PBS, alternatively in 100 μg/ml human transferrin/PBS or in other embodiments in 100 μg/ml BSA/PBS, in 0.5M sucrose or 0.5M trehalose.

Cell Culture Preparation

Laminated cerebellar cortices of the two hemispheres were explanted from a P3, P4, P7 or P8 Wistar rat, cut into small pieces in GBSS with 0.65% D(+)glucose solution, and triturated by a 0.4 mm gauge needle and subsequently pressed through a 125 μm pore size sieve. The obtained microexplants were centrifuged (60×g) 2 times for a medium exchange into serum-free BSA-supplemented START V-medium (Biochrom). Finally, the microexplants were reconstituted in 500 μl STARTV-medium. For culturing, 38 μl of the cell suspension was incubated for 1 hour on a poly-D-lysine-coated cover slip in a 35 mm Petri dish under an atmosphere comprising 5% $CO_2$ in air and 100% humidity at 34° C. Subsequently, the injuring toxins (as described below), NRP analogues and 1 ml of STARTV-medium were added, and the cultures were evaluated after 2-3 days of culture.

For immunohistochemistry and neuronal migration experiments, cerebellar microexplants were fixed after 2-3 days in culture after the following regime: microexplants were fixed by 2-minute, serial treatment with 0.4%; 1.2%; 3% paraformaldehyde, respectively, followed by a 5 min incubation in 4% paraformaldehyde/0.25% glutaraldehyde in 0.1 M sodium phosphate (pH 7.4).

Effects of NRP Compounds on Toxin-Induced Neural Injury

Oxidative stress can result in neurodegeneration. This is one possible mechanism for the symptoms observed in human disorder with Huntington's disease. The oxidative stress-producing toxin, 3-nitropropioinic acid (3-NP) has been previously shown to produce effects in experimental animals that mimic those effects seen in human beings with Huntington's disease. Thus, studies of therapeutic drugs in experimental animals with 3-NP induced neurotoxicity are predictive of effects of those drugs in treating human beings with Huntington's disease or other disorders characterized by oxidative stress.

General methods for toxicological and drug administration experiments were designed such that 1/100 parts of toxin and neuroprotective drug were administered simultaneously to the freshly prepared cerebellar microexplants. Glutamate was prepared as a 50 mM stock solution in MilliQ water while 50 mM 3-nitropropionic acid (3-NP) was pH-adjusted (pH 6.8-7.2) in MilliQ water. The concentrations of the oxidative stress inducing toxin, 3-nitropropionic acid (3-NP), and the excitotoxin, glutamate, in the assay were at concentrations of 0.5 mM each. Lyophilized NRP peptides were reconstituted in PBS or 100 μg/ml human transferrin as a 10 μM stock solution. Subsequently, serial dilutions were made. Cerebellar microexplants were cultivated for 48-72 hours at 34° C., 5% $CO_2$ in air and 100% humidity before they were fixed by increasing amounts of paraformaldehyde (0.4%, 1.2%, 3% and 4%—each treatment 2-3 min).

Using the toxins described above, cerebellar explants were exposed for 24 hours, at the beginning of culturing to dilutions of NRP (survival assay) or NRP and 0.1 μM BrdU (proliferation assay). Subsequently, 80% of the medium was changed without addition of new toxins and NRPs. The cerebellar cultures were fixed as described above after 3 days in vitro. The detection of the incorporated BrdU level is performed as described previously.

Data Reduction and Statistical Analysis

For statistical analysis of survival, four fields (each field having an area of 0.65 $mm^2$) of each fixed cerebellar culture with the highest cell densities were chosen, and cells displaying neurite outgrowth were counted (survival assay).

Results
Neuroprotection

NRP analogues promoted increased neuronal survival in explants treated with 3-NP (see Examples 2, 3 and 4).

Example 2

Promotion of Neural Cell Survival by NRP Compounds

We studied effects of different concentrations of SEQ ID NO:1, and SEQ ID NO:5 of this invention on cell cultures prepared according to Example 1 above. SEQ ID NO:1 and SEQ ID NO:5 have the same amino acid sequence, with the exception that the Alanine (A) in position 9 of the amino acid sequence of SEQ ID NO:1 was replaced by aminoisobutyric acid (Aib), thus producing a compound having the sequence shown in SEQ ID NO:5. One can appreciate that in addition to the change in linear structure of the peptide, Aib replacement of Alanine can stabilize the beta-turn, and thus, produce a peptide having different 3-dimensional structure and different mobilities about certain bonds compared to the un-substituted peptide.

We exposed cell cultures to vehicle alone (open column) the neurotoxin 3-NP alone (shaded column) to 3-NP plus different concentrations of SEQ ID NO:5 (hatched columns) or to 3-NP plus different concentrations of a non-substituted NRP, SEQ ID NO:1 (dark shaded column). We then counted the numbers of cells having neurites as an indicator of neuronal cell survival.

Figure 1:
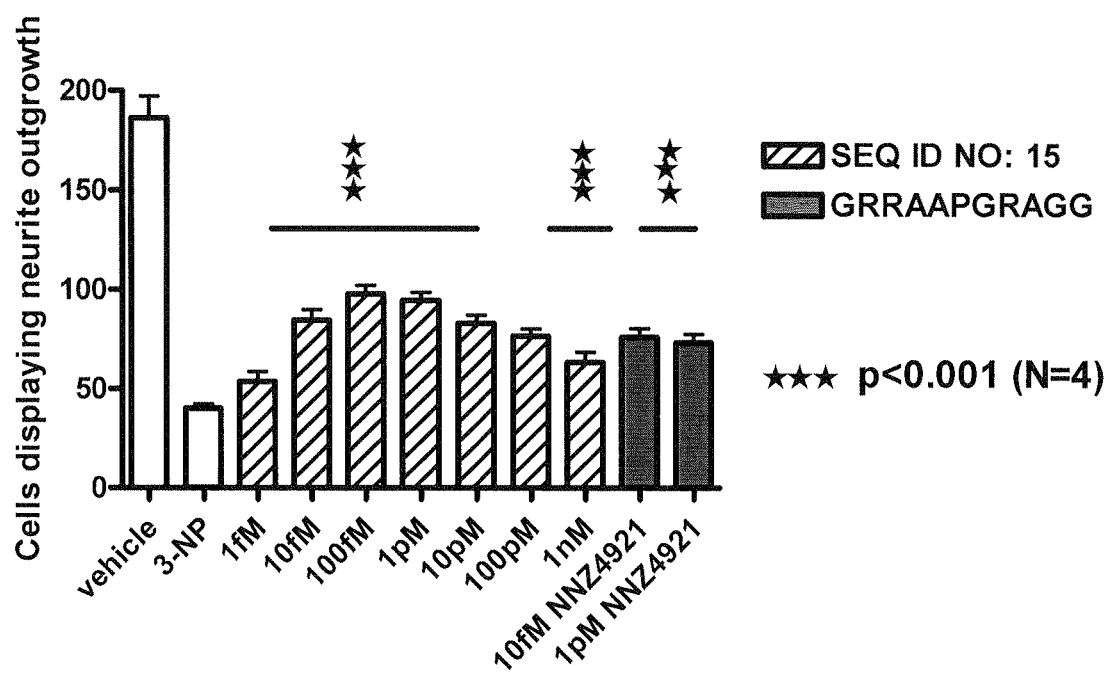
FIG. 1 depicts a graph of neuroprotective effects of two NRPs, SEQ ID NO: 5 of this invention and SEQ ID NO:1 in cell cultures exposed to the neurotoxin 3-NP.

FIG. 1 depicts a graph of results of these studies. 3-NP alone produced profound loss of cells displaying neurites compared to vehicle-treated controls, indicating that the compound is indeed neurotoxic. The peptide having the sequence SEQ ID NO:1 at concentrations of 10 fM or 1 pM significantly decreased the neurotoxic effects of 3-NP (mean±SEM; $p<0.001$; n=4). Similarly, SEQ ID NO:5 decreased 3-NP-induced neurotoxicity in a concentration dependent fashion, with a threshold of below about 1 fM and a maximal effect at a concentration of about 100 fM (mean±SEM; $p<0.001$; n=4 each).

From this study, we conclude that SEQ ID NO:5 is neuroprotective. This result means that SEQ ID NO:5 can be a valuable therapeutic NRP compound for treating neural degeneration in humans suffering from neurological disorders. Further, because oxidative stress is known to induce neurodegeneration similar to the neurodegeneration observed in human beings with Huntington's disease, synthetic NRP compounds of this invention can be used to treat human beings with neurodegeneration caused by oxidative stress.

Example 3

Stability and Neuroprotective Effects of Un-Substituted NRP Compounds

To determine the stability of NRPs of this invention in storage, we carried out a series of studies using SEQ ID NO:1. In this study, we synthesized SEQ ID NO:1 and then stored the peptide at temperatures of either $-20°$ C. or $-4°$ C. for nine (9) weeks. We then tested the NRP for efficacy in protecting cerebellar neurons against the neurotoxic effect of 3-NP as described above. Cerebellar explants were treated with vehicle alone (open column), the neurotoxic agent 3-NP alone (light stippled column), or 3-NP plus four concentrations of SEQ ID NO:1 that had been stored for 9 weeks at $-20°$ C., or at $-4°$ C.

Figure 2:
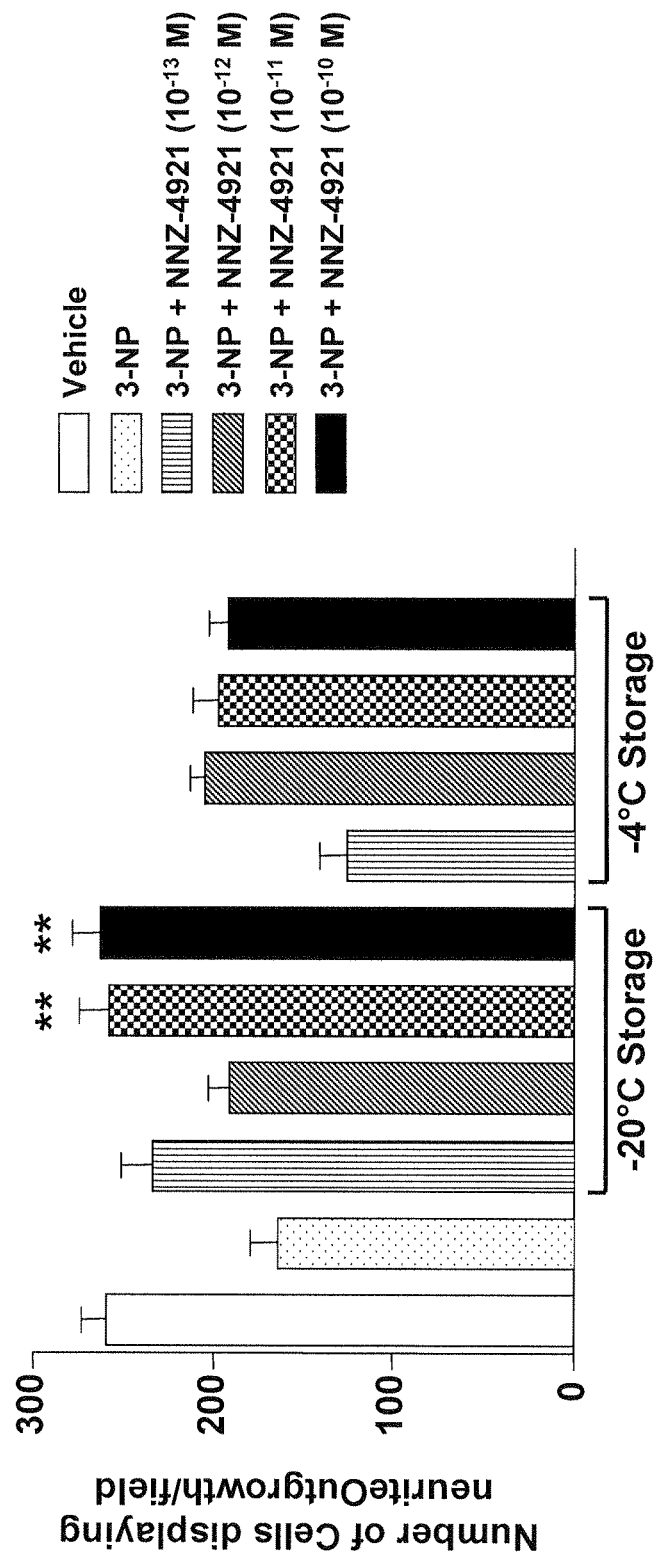
FIG. 2 depicts a graph of results of studies of neuroprotective effective of SEQ ID NO:1 in which the peptide was stored at either −20° C. or −4° C.

FIG. 2 depicts results of these studies. Cerebellar explants treated with 3-NP alone (light stippled bar) showed fewer cells exhibiting neurites compared to vehicle-treated control explants (open bar). SEQ ID NO:1 that had been stored at $-20°$ C. exhibited neuroprotective effects at all concentrations tested (from $10^{-13}$ M; 100 fM to $10^{-10}$ M; 100 pM), with statistically significant effects observed at concentrations of $10^{-11}$ M and $10^{-10}$ M.

In contrast, SEQ ID NO:1 stored at a temperature of $-4°$ C. produced little decrease in neurotoxic effect of 3-NP. We conclude from this study that the unsubstituted NRP loses activity over the 9-week period with storage at $-4°$ C., and that storing SEQ ID NO:1 at $-20°$ C. can protect its potency.

Example 4

Stability and Neuroprotective Effects of Substituted NRPs

In this study, we determined the stability of a substituted NRP, SEQ ID NO:5, in different storage conditions and at different concentrations as with Example 3 above. We synthesized SEQ ID NO:5 and then stored the peptide for 9 weeks at a temperature of either $-20°$ C. or $-4°$ C. We then tested the efficacy of SEQ ID NO:5 in decreasing the neurotoxic effect of 3-NP as described in Examples 2 and 3 above.

Figure 3:
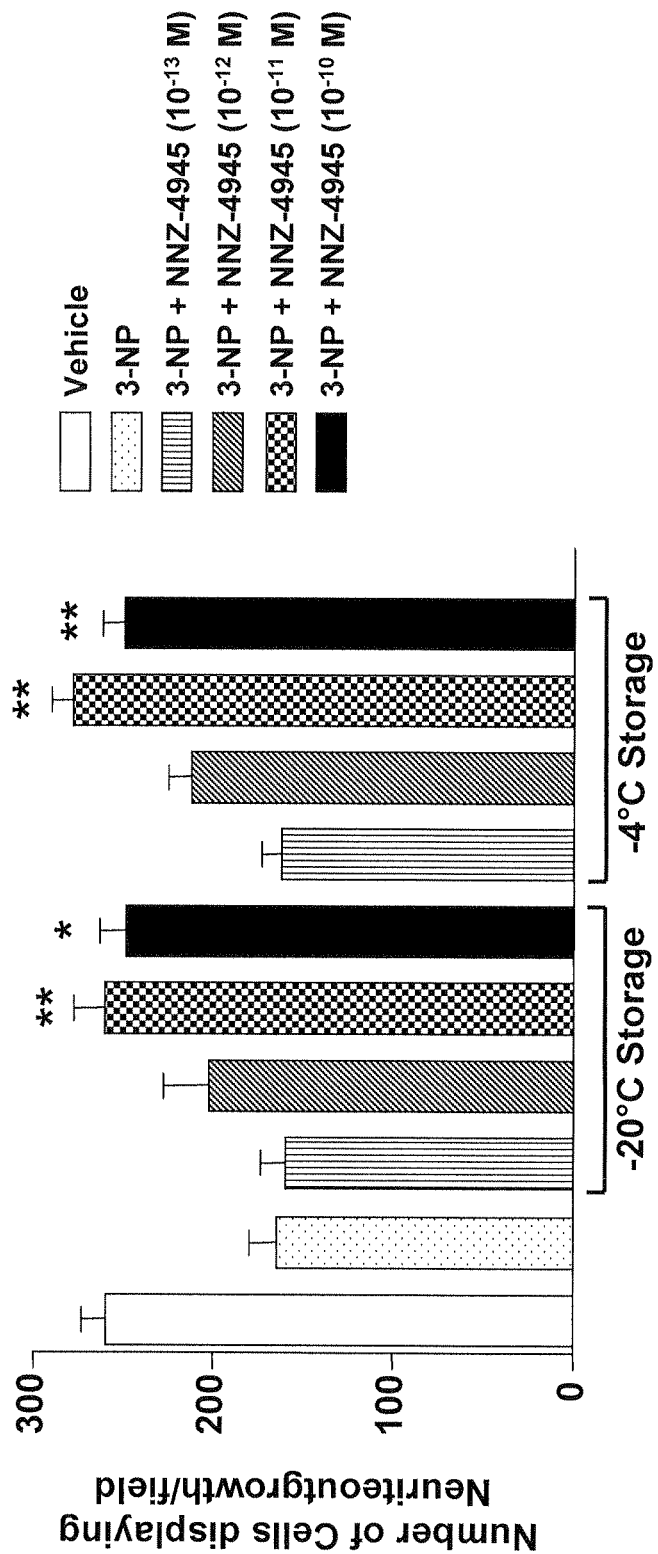
FIG. 3 depicts a graph of results of studies of neuroprotective effects of SEQ ID NO: 5 of this invention in which the peptide was stored at either −20° C. or −4° C.

FIG. 3 depicts a graph of these studies. Cerebellar explants were treated with vehicle alone (open column), 3-NP alone (light stippled column) or 3-NP plus concentrations of SEQ ID NO:5 in four concentrations ranging from $10^{-13}$ M to $10^{-10}$ M) that had been stored at either $-20°$ C. or at $-4°$ C. When stored at $-20°$ C., SEQ ID NO:5 produced neuroprotective effects similar to those found for SEQ ID NO:1 that had been stored at $-20°$ C., as shown in Example 3 and depicted in FIG. 2.

We surprisingly found that even when stored at $-4°$ C., SEQ ID NO:5 retained its neuroprotective effect. In fact, the degree of neuroprotection provided by SEQ ID NO:5 after storage at $-4°$ C. was not statistically different from the degree of neuroprotection provided after storage at $-20°$ C. This result was completely unexpected based on studies of SEQ ID NO:1 shown above. The increased stability of the NPR having SEQ ID NO:5 means that this compound will be more suitable for storage and transportation under commonly used conditions.

Example 5

Neuroprotective Effects of Un-Substituted and Substituted NRPs

Figure 4:
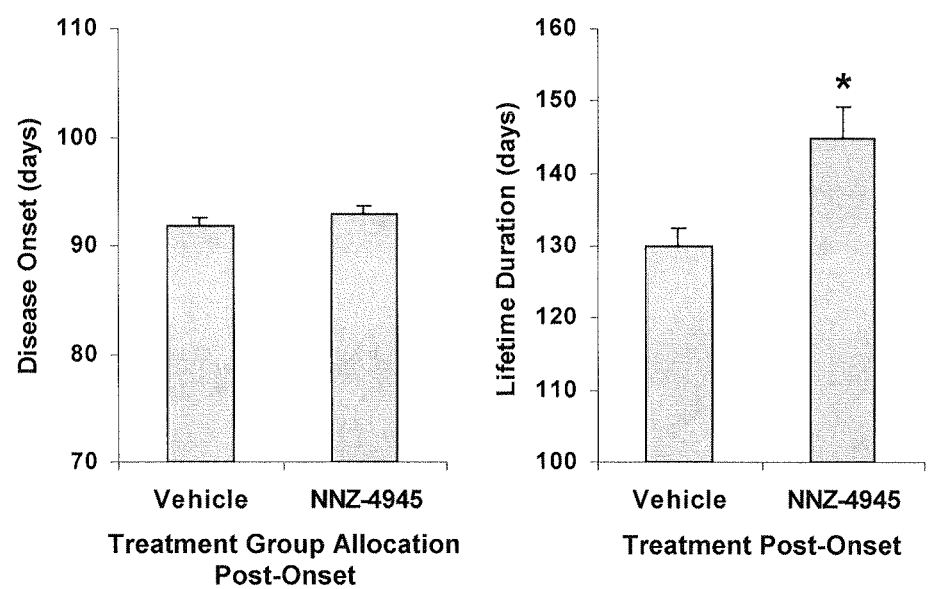
FIG. 4 depicts a graph of results of an enlarged study of neuroprotective effects of SEQ ID NO:5 of this invention and SEQ ID NO:1 in cell cultures treated with the neurotoxin 3-NP, similar to those shown in FIG. 1.

In a larger set of data obtained using the methods of Example 1, we confirmed the results shown in FIG. 1. FIG. 4 depicts a graph of results of studies of cerebellar microexplants treated with the neurotoxin 3-NP, demonstrating neuroprotection by SEQ ID NO:5 and SEQ ID NO:1 in a study of 6 in each group. We conclude that SEQ ID NO:1 and SEQ ID NO:5 protect neurons from dying after exposure to the neurotoxin 3-NP. We also conclude that SEQ ID NO:5 and SEQ ID NO:1 can be useful therapeutic agents in treating human beings suffering from neurotoxicity.

Example 6

Therapeutic and Prophylactic Effects of NRP Analogues in a Model of Multiple Sclerosis To determine whether NRPs have an impact on chronic inflammation in the CNS that leads to severe axonal damage and subsequent lesions (such as in multiple sclerosis; MS), we tested NRPs in a mouse model of experimental autoimmune encephalitis (EAE) that mimics the severe progressive state of MS, using myelin oligodendrocyte glycoprotein (MOG) as the immunogen.

Methods and Materials

Animals

Female mice, 6-8 weeks-old, strain C57B1/6J weighing an average of 24 gms each were used.

NRP Preparation

The peptide having the sequence: $NH_2$—REGR-RDAPGRAGG-$NH_2$ SEQ ID NO:12 (also known as SEQ ID NO: 30 disclosed in U.S. patent application Ser. No. 10/976, 699), was supplied by Auspep (Australia). The peptide SEQ ID NO:12 was supplied with an amidated C-terminus, and was more than 95% pure as determined by MALDI-MS spectroscopy.HPLC. The sequence was confirmed by mass spectroscopy. The peptide was stored lyophilized at a temperature of –80° C. under argon gas until use. The peptide was reconstituted in PBS on the day of use.

Induction EAE

A 200 μul L of an emulsion containing 200 μg of the encephalitogenic peptide MOG35-55 MEVGWYRSPFSRV-VHLYRNGK SEQ ID NO:13 was obtained from C S Bio Co. USA) in complete Freund adjuvant (Difco, Detroit, USA) containing 800 μug *Mycobacterium tuberculosis* (Difco, Detroit, USA) was injected subcutaneously into one flank. Mice were immediately injected intraperitoneally with 400 ng pertussis toxin (List Biological Laboratories, USA) and again 48 hours later.

Treatment

Therapeutic

At the peak of the disease (day 17 after MOG-immunization) animals were treated with SEQ ID NO: 12 intraperitoneally (i.p.) for 14 days with a daily dose of 0.1 μg peptide/animal (4.16 μg/kg).

Assessment of Neurological Impairment

Mice were monitored daily and neurological impairment was scored on an arbitrary clinical score as follows: 0, no clinical sign; 1, flaccid tail; 2, hind limb weakness; 3, hind limb paralysis; 4, hind limb weakness and fore limb weakness; 5, paraplegia; 6, death.

Results

Therapeutic Effects of NRPs on EAE in Mice

Figure 5:
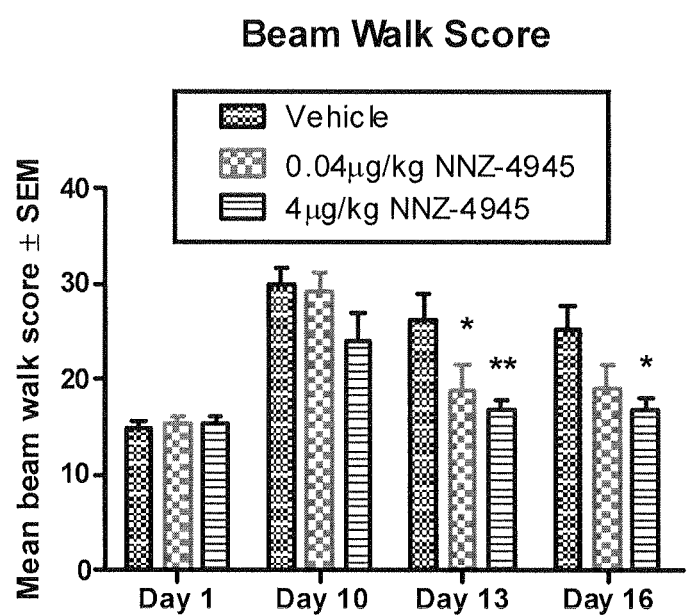
FIG. 5 depicts a graph showing significant long-term effects of sequence REGRRDAPGRAGG (SEQ ID NO:12) of this invention to decrease the severity of motoric impairment in animals with EAE, when the synthetic NRP was administered at the peak of the disease. Score 1 is the lowest score and implies a flaccid tail only, while the higher scores imply weakness (score 2) or complete paralysis of the hind legs (score 3). Kruskal-Wallis-test was used for statistical analysis; ** $p<0.01$ versus treatment day 1 score (data expressed as mean±SEM).

The outcome 37 days after the first NRP treatment is shown in FIG. 5. There is a significant therapeutic effect of SEQ ID NO: 12 when peripherally administered. A similar drug effect has been shown for the neuroregenerative compound EPO in a combination therapy with methylprednisolone. The disadvantage of EPO is its large size as it cannot easily be synthesized or administered. We conclude that NRP has significant long-term potential to decrease the severity of motoric impairment occurring in the EAE disease model of MS when administered as therapeutic drug at the peak of the disease. Score 1 is the lowest score and implies a flaccid tail only while the higher scores imply weakness (score 2) or complete paralysis of the hind legs (score 3). ** $p<0.01$ versus treatment day 1 score.

Example 7

Effects of NRP Analogues in Animals with Peripheral Neuropathy

To determine if NRP analogues of this invention can be useful therapeutic agents for treating peripheral neuropathy, we carried out a series of studies in rats with peripheral neuropathy induced by pyridoxine.

We demonstrated that $NH_2$-$G^1$RRAAPGR-Aib-$GG^{11}$-$NH_2$ (SEQ ID NO:5) at very low doses applied as a single bolus per day can attenuate motor deficits in animals treated with toxic doses of pyridoxine.

Materials and Methods

Male Sprague-Dawley rats were used and were weighed 278-349 g at the commencement of intoxication with pyridoxine chloride. Before intoxication, rats were habituated to walk across a beam at daily intervals for a week.

Experiment I: Rats were administered 400 mg/kg pyridoxine chloride dissolved in sterile distilled water adjusted to neutral pH intraperitoneally (i.p) twice daily for 8 days and concurrently the peptide having the sequence SEQ ID NO:5 was administered i.p. for at total of 10 days. The rats were observed for a total of 29 days.

Experiment II: Rats were administered a higher dose of pyridoxine (1200 mg/kg/day) over a shorter period of time. Pyridoxine chloride dissolved in sterile distilled water adjusted to neutral pH was administered i.p. to the rats at a dose of 600 mg/kg twice daily for 4 days. Concurrently the peptide having the sequence SEQ ID NO:5 was administered for 4 days. On day 5, rats were tested for motor deficits.

Motor deficits after pyridoxine intoxication and effects of SEQ ID NO:5 were analyzed using a precision beam walk. Seven subsequent foot steps across the 1.5 m long beam were videotaped and according to the positioning of the foot tarsus, these steps were scored between 1 to 4 (1—hind leg tarsus above the beam median; 2—tarsus was touching the upper half of beam medium; 3-tarsus was touching the lower half of beam median and 4—tarsus below the beam median). The score results of all seven steps were added together. A score of 30 was given if the animal was only able to stand on the beam but was unable to walk. In the event of inability to stand on the beam a score of 32 was awarded.

Treatment Groups

Experiment I: The two concentrations tested for SEQ ID NO:5 were 40 ng/kg/day and 4 μg/kg/day.

Experiment II: Saline and SEQ ID NO:5 at a dose of 4 μg/kg/day were tested.

Statistics Analysis

Motor deficit data were assessed by two-way analysis of variance and Bonferroni post-hoc test. Statistical significance was concluded if $p<0.05$ between drug treatment cohorts and vehicle treatment.

Results

Figure 6:
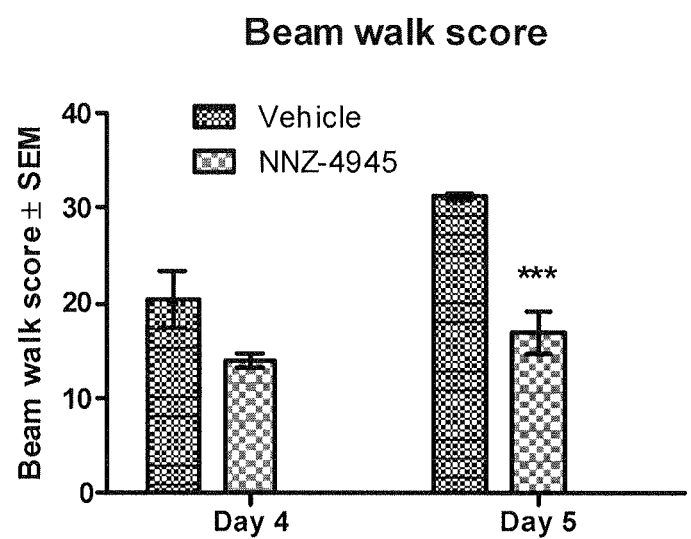
FIG. 6 depicts a graph of results of beam walking scores for rats with peripheral neuropathy induced by pyridoxine (800 mg/kg/day) and treated with either vehicle or SEQ ID NO:5 of this invention at two different doses.

Experiment I:

Four days after cessation of pyridoxine-intoxication both SEQ ID NO:5-treated rat cohorts show attenuated motor deficits (low dosage: $p<0.05$; high dosage: $p<0.01$) compared to the vehicle-treated group. At day 16 after start of pyridoxine-intoxication the high dose SEQ ID NO:5 group had still significantly less motor deficits than the control group ($p<0.05$). (FIG. 6).

Experiment II:

Four subsequent days of high-dosage pyridoxine-intoxication lead to substantial motor deficits in the control group of rats. On day 5 the SEQ ID NO:5-treated rat group (dosage: 4 μg/kg/day) showed highly significantly attenuation of motor deficits ($p<0.001$) (FIG. 7).

Conclusions

We conclude that SEQ ID NO:5 showed highly significant and clinically substantial attenuation of motor deficits pyridoxine-induced peripheral neuropathy. We also conclude that at a dose of 4 μg/kg/day, SEQ ID NO:5 was well tolerated. The 4 μg/kg/day concentration worked equally well in the more chronic model of pyridoxine intoxication (800 mg/kg/day for 8 days) and the acute pyridoxine intoxication induced by 1200 mg/kg/day administered for 4 days.

We further conclude from these studies that SEQ ID NO:5 can be effective treatment for peripheral neuropathies in human beings.

Example 8

Effect of SEQ ID NO:5 on Animals With Amytrophic Lateral Sclerosis (ALS)

In this series of studies, we examined the effects of SEQ ID NO:5 on mice having a genetic defect (SOD-1) that produces a motor neuron disease similar to that in humans with ALS Animals with this disorder show a progressive loss of motor coordination over time, and ultimately die prematurely of the disease. This animal system is useful in studying effects of agents potentially useful in treating ALS in human beings. Thus, results obtained are highly predictive of results obtained in humans with ALS.

Methods

Mice were randomly allocated to receive either vehicle or SEQ ID NO:5 from the point of disease onset onwards. Disease onset in each treatment allocation group was not significantly different: 92-93 days.

SEQ ID NO:5 treatment (40 µg/kg, given 1/day, i.p. (FIG. 8A) or 0.4 µg/kg, given 1/day, i.p. (FIG. 8B)) was started at the day of onset of the disease.

Results

In two studies, SEQ ID NO:5 treatment resulted in a significant extension of lifetime in the mice suffering from the ALS-like disorder (FIGS. 8A and 8B). A daily dose of 40 µg/kg i.p. SEQ ID NO:5 significantly promoted longevity following disease onset. FIGS. 8A and 8B show Kaplan-Meier survival probability curves for the SOD-1 mutant (ALS) transgenic mice.

The vehicle-treated animals began to die at day 120, and were all dead by day 143 (Study 1; FIG. 8A; solid line) Similarly, in Study 2 (FIG. 8B; solid line), vehicle-treated animals began to die at day 120 asn were all dead at day 154 (FIG. 8B; solid line).

In contrast, in Study 1 (FIG. 8A; dashed line) SEQ ID NO:5-treated mice began dying later (at day 131) than vehicle-treated animals and lived longer (up to 156 days) Significantly, the two Kaplan-Meier curves did not overlap (FIG. 8A; 40 µg/kg SEQ ID NO:5; p<0.01 compared to survival of animals treated with vehicle alone). In Study 2 animals treated with SEQ ID NO:5 (FIG. 8B; dashed line; 0.4 µg/kg) began to die later (at day 125) than vehicle-treated animals (FIG. 8B; solid line) and in general, lived longer (up to 189 days: FIG. 8B; dashed line; SEQ ID NO:5.

Conclusions

We conclude from these studies that SEQ ID NO:5 is an effective agent that has unexpectedly improved stability compared to its un-substituted counterpart. We also conclude that stabilizing the beta-turn of an NRP can improve therapeutic efficacy and can improve stability, both of which can improve therapeutic utility of NRP analogues. The unexpected findings that substituted NRP analogues have both improved potency and improved stability indicates that the NRP analogues can be valuable therapeutic alternatives for treating a variety of conditions characterized by neurodegeneration.

Therefore, NRP analogues of this invention can be useful in treating acute as well as chronic neurodegenerative disorders including ALS, neurotoxicity, neurodegeneration associated with oxidative stress, autoimmune disorders, traumatic brain injury and other neurological diseases and conditions. Further, we conclude that NRP analogues can have beneficial therapeutic effects in situations where loss of neurological function is a symptom.

Example 9

NRP Analogue-Mediated Migration in Physiological (Injury-Free) Conditions

An NRP analogue is tested for migration-inducing/chemoattractive activity on mouse neural stem cells in a haptotactic migration assay as described below.

Methods

Initial NRP Coating

Control wells of Transwell plates (Corning) with 12 µm pore size are coated in 1.5 ml of the BSA/PBS vehicle. Remaining plates are coated using 0.1 ng/ml of NRP analogue (prepared in PBS containing 10 ug/ml BSA).

Extracellular Matrix Coating

Laminin (7 µg/ml) is used as extracellular matrix (ECM) coating for mouse primary stem cells. The matrix is incubated at 37° C.; 5% $CO_2$ for 2 hrs at room temperature. The cells are seeded onto the inserts (30,000 cells per well). Plates are fixed at 1-2 days in vitro (DIV).

Coating of Inserts

A 5 ug/mL PDL/PLL mixture (in PBS) is used to coat inserts. Subsequently the inserts are rinsed with MilliQ water.

Cell Fixation

Inserts are discarded and wells fixed in successive dilutions of PFA (0.4, 1.2, 3 and 4%) for 3-5 min in each dilution. The wells are rinsed and stored in successive dilutions of PFA (0.4, 1.2, 3 and 4%) 3-5 min in each dilution. The wells are rinsed and stored in PBS until counting. All cells that display neurite outgrowth and traveled to the bottom chamber are counted as migrating cells.

Results

More cells migrate in plates treated with NRP analogue than migrated in plates without NRP analogue. NRP analogues can induce neuronal cell migration, and that they each can be used to treat neurodegeneration associated with neural injury or disease.

Example 10

NRP Analogue-Mediated Migration in Injury Conditions

An NRP analogue is tested for migration-inducing/chemoattractive activity on mouse neural stem cells in a haptotactic migration assay in injury conditions, as described below.

Methods

Production of a Monolayer of Astrocytes

P1 (postnatal day 1) Wistar or Sprague Dawley rats are sacrificed by decapitation. Cortical hemispheres are removed and collected into separate tubes containing 4 ml DMEM—1 cortex per tube. The tissue is mechanically triturated. Cells are transferred into medium using a sterile pipette and filtered through a 100 um cell strainer into a 50 ml centrifuge tube. Each tube is stocked up to 50 ml with DMEM. The tubes are centrifuged for 5 mins at 350×g at 22° C. The cells are resuspended in 40 ml of DMEM+10% FBS. The cells are then seeded into a 12-well plate+5 nM ocadaic acid (to remove neurons by inducing apoptotic cell death) and incubated at 37° C./10% $CO_2$ for 24 hrs in a Boyden Chamber.

The medium+FBS is replaced after 1 day with fresh DMEM+ 10% FBS. The cell growth is monitored until confluency (14-18 days).

Pharmacological and Mechanical Injury

Induction of injuries to the astrocytic monolayer is accomplished using the pharmacological agent transforming growth factor β1 (TGFβ1) and simultaneous mechanical scratching of the monolayer in order to activate astrocytics. 10 ng/ml TGFβ1 is administered to the astrocytic monolayer for 24 hrs. Additionally, astrocytic cultures re mechanically injured by a scalpel (one scratch throughout the bottom of the well).

Seeding of Pre-Labelled Stem Cells

Undifferentiated fluorescein diacetate-labelled embryonic mouse neural stem cells (NSCs) are seeded into Poly-D-Lysine (PDL—5 µg/ml) coated inserts. The lower compartment of the Boyden chamber receives 100 fM of an NRP analogue.

Cell Fixation

Inserts are discarded and wells fixed in successive dilutions of PFA (0.4, 1.2, 3 and 4%) for 3-5 min in each dilution. The wells are rinsed and stored in successive dilutions of PFA (0.4, 1.2, 3 and 4%) 3-5 min in each dilution. The wells are rinsed and stored in PBS until counting. All cells that display neurite outgrowth and traveled to the bottom chamber are counted as migrating cells.

Analysis

Migrated stem cell number of labelled cells re analysed after 24 hrs by a fluorescence-based computerized imaging system (Discovery-1).

Results

NRP analogues stimulate more stem cells to migrate than vehicle-treated controls. We conclude that NRP analogue induces neuronal stem cell migration, and that NRP analogues can be useful to treat neurodegeneration associated with neural injury or disease.

References

[1] Schaumburg H, Kaplan J, Windebank A, Vick N, Rasmus S, Pleasure D, Brown M J (1983) Sensory neuropathy from pyridoxine abuse. A new megavitamin syndrome. N. Engl. J. Med. 309: 445-448.

[2] Krinke G, Naylor D C, Skorpil V (1985) Pyridoxine megavitaminosis: an analysis of the early changes induced with massive doses of vitamin B6 in rat primary sensory neurons. J. Neuropathol. Exp. Neurol. 44: 117-129.

[3] Windebank A J, Low P A, Blexrud M D, Schmelzer J D, Schaumburg H H (1985) Pyridoxine neuropathy in rats: specific degeneration of sensory axons. Neurology 35: 1617-1622.

[4] Albin R L, Albers J W, Greenberg H S, Townsend J B, Lynn R B, Burke Jr. J M, Alessi A G (1987) Acute sensory neuropathy-neuronopathy from pyridoxine overdose. Neurology 37: 1729-1732.

[5] Dalton K, Dalton M J (1987) Characteristics of pyridoxine overdose neuropathy syndrome. Acta Neurol. Scand. 76: 8-11.

[6] Xu Y, Sladky J T, Brown M J (1989) Dose-dependent expression of neuropathy after experimental pyridoxine intoxication. Neurology 39: 1077-1083.

[7] Perry T A, Weerasuriya A, Mouton P R, Holloway H W, Greig N H (2004) Pyridoxine-induced toxicity in rats: a stereological quantification of the sensory neuropathy. Exp Neurol. 190: 133-144.

[8] Helgren M E, Cliffer K D, Torrento K, Cavnor C, Curtis R, Distefano P S, Wiegand S J, Lindsay R M (1997) Neurotrophin-3 administration attenuates deficits of pyridoxine-induced large-fiber sensory neuropathy. J. Neurosci. 17: 372-382.

[9] Callizot N, Warter J-M, Poindron P (2001) Pyridoxine-induced neuropathy in rats: a sensory neuropathy that responds to 4-methylcatechol. Neurobiol. Dis. 8: 626-635.

[10] Perry T A, Holloway H W, Weerasuriya A, Mouton P R, Duffy K, Mattinson J A, Greig N H (2007) Evidence of GLP-1-mediated neuroprotection in an animal model of pyridoxine-induced peripheral sensory neuropathy. Exp. Neurology 203: 293-303.

[11] Jakobsen J, Lundbæk K. (1976) Neuropathy in experimental diabetes: an animal model. Br. Med. J. 2: 278-279

[12] Bell R H, Hye R J (1983) Animal models of diabetes mellitus: physiology and pathology. J. Surg. Res. 35: 433-460.

[13] Mattingly G E, Fischer V W. (1983) Peripheral neuropathy following prolonged exposure to streptozotocin-induced diabetes in rats: a teased nerve fiber study. Acta Neuropathol. 59: 133-138.

[14] Szkudelski T (2001) The mechanism of alloxan and streptozotocin action in B cells of the rat pancreas. Physiol. Res. 50: 536-546.

[15] Schmeichel A M, Schmelzer J D, Low P A (2003) Oxidative injury and apoptosis of dorsal root ganglion neurons in chronic experimental diabetic neuropathy. Diabetes 52: 165-171.

[16] Tomlinson D R, Gardiner N J (2008) Glucose neurotoxicity. Nature Neurosci. Rev. 9:36-45.

[17] Wuarin-Bierman L, Zahnd G R, Kaufmann F, Burcklen L, Adler J. (1987) Hyperalgesia in spontaneous and experimental animal models of diabetic neuropathy. Diabetologia. 30: 653-658.

[18] Courteix C, Eschalier A, Lavarenne J. (1993) Streptozocin-induced diabetic rats: behavioural evidence for a model of chronic pain. Pain. 53: 81-88.

[19] Dyck P J, Giannini C. (1996) Pathologic alterations in the diabetic neuropathies of humans: a review. J. Neuropathol. Exp. Neurol. 55: 1181-1193.

[20] Yagihashi S, Yamagishi S-I, Wada R. (2007) Pathology and pathogenic mechanisms of diabetic neuropathy: correlation with clinical signs and symptoms. Diab. Res. Clin. Prac. 77S: S184-S189.

[21] Chong M S, Hester J (2007) Diabetic painful neuropathy. Current and future treatment options. Drugs 67: 569-585.

[22] Quasthoff S, Hartung H P (2002) Chemotherapy-induced peripheral neuropathy. J. Neurol. 249: 9-17.

[23] Windebank A J, Grisold W. (2008) Chemotherapy-induced neuropathy. J. Peripher. Nerv. Syst. 13: 27-46.

[24] Gregg R W, Molepo J M, Monpetit V J, Mikael N Z, Redmond D, Gadia M, Stewert D J. (1992) Cisplatin neurotoxicity: the relationship between dosage, time, and platinum concentration in neurologic tissues, and morphologic evidence of toxicity. J. Clin. Oncol. 10: 795-803.

All patents, patent applications and other publications are incorporated herein fully by reference as if separately so incorporated. The Sequence Listing appended to this application is also incorporated herein fully by reference.

A person of ordinary skill in the art will not have to undertake undue experimentation, taking account of that skill and the knowledge available, and of this disclosure, in developing one or more suitable synthetic compounds. All such compounds and methods for their manufacture and use are considered to be part of this invention.

Compounds and compositions of this invention find industrial use in many aspects of commerce, including pharmaceutical manufacturing, formulation, and sale. Methods of using compounds and compositions of this invention find industrial use in medical fields of neurology, and in particular, for treatment of neurological disorders in animals and human beings.

What is claimed is:

1. A method for the treatment of peripheral neuropathy, multiple sclerosis and amyotrophic lateral sclerosis in an animal, comprising administering to said animal a pharmaceutically effective amount of a neural regeneration peptide (NRP) compound comprising an amino acid sequence selected from the group consisting of SEQ ID NO:4, SEQ ID NO:5 and SEQ ID NO:6, or a pharmaceutical composition comprising a NRP compound comprising an amino acid sequence selected from the group consisting of SEQ ID NO:4, SEQ ID NO:5 and SEQ ID NO:6 and a pharmaceutically acceptable excipient.

2. The method of claim 1, wherein said NRP compound consists of the sequence SEQ ID NO:5.

3. The method of claim 1, wherein said NRP compound consists of the sequence SEQ ID NO:6.

* * * * *

SEQUENCE LISTING

<160> NUMBER OF SEQ ID NOS: 13

<210> SEQ ID NO 1
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 1

Gly Arg Arg Ala Ala Pro Gly Arg Ala Gly Gly
1               5                   10

<210> SEQ ID NO 2
<211> LENGTH: 4
<212> TYPE: PRT
<213> ORGANISM: Homo sapiens

<400> SEQUENCE: 2

Ala Pro Gly Arg
1

<210> SEQ ID NO 3
<211> LENGTH: 4
<212> TYPE: PRT
<213> ORGANISM: Homo sapiens

<400> SEQUENCE: 3

Arg Ala Gly Gly
1

<210> SEQ ID NO 4
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (11)..(11)
<223> OTHER INFORMATION: AMIDATION

<400> SEQUENCE: 4

Gly Arg Arg Ala Xaa Pro Gly Arg Ala Gly Gly
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (11)..(11)
<223> OTHER INFORMATION: AMIDATION

<400> SEQUENCE: 5

Gly Arg Arg Ala Ala Pro Gly Arg Xaa Gly Gly

```
1               5                   10
```

<210> SEQ ID NO 6
<211> LENGTH: 11
<212> TYPE: PRT
<213> ORGANISM: Artificial sequence
<220> FEATURE:
<223> OTHER INFORMATION: Synthetic peptide

<400> SEQUENCE: 6

```
Gly Arg Arg Ala Ala Pro Gly Arg Ala Asn Gly
1               5                   10
```

<210> SEQ ID NO 7
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 7

```
Arg Arg Ala Ala Pro Gly Arg Ala Gly Gly
1               5                   10
```

<210> SEQ ID NO 8
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-argenine

<400> SEQUENCE: 8

```
Gly Arg Asp Arg Ala Ala Pro Gly Arg Ala Gly Gly
1               5                   10
```

<210> SEQ ID NO 9
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: DISULFID
<222> LOCATION: (1)..(13)

<400> SEQUENCE: 9

```
Cys Gly Arg Arg Ala Ala Pro Gly Arg Ala Gly Gly Cys
1               5                   10
```

<210> SEQ ID NO 10
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: DISULFID
<222> LOCATION: (1)..(11)

```
<400> SEQUENCE: 10

Cys Arg Arg Ala Ala Pro Gly Arg Ala Gly Cys
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 11

Gly Arg Arg Ala Ala Pro Gly Arg Ala Gly Gly
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: AMIDATION

<400> SEQUENCE: 12

Arg Glu Gly Arg Arg Asp Ala Pro Gly Arg Ala Gly Gly
1               5                   10

<210> SEQ ID NO 13
<211> LENGTH: 21
<212> TYPE: PRT
<213> ORGANISM: Mycobacterium tuberculosis

<400> SEQUENCE: 13

Met Glu Val Gly Trp Tyr Arg Ser Pro Phe Ser Arg Val Val His Leu
1               5                   10                  15

Tyr Arg Gln Gly Lys
            20
```